United States Patent
Lee et al.

(10) Patent No.: US 8,987,429 B2
(45) Date of Patent: Mar. 24, 2015

(54) GO-GD-DTPA COMPLEX, PREPARATION METHOD THEREOF, AND MRI CONTRAST AGENT COMPRISING THE SAME

(75) Inventors: Hyo Young Lee, Suwon-si (KR); Luyang Wang, Suwon-si (KR)

(73) Assignee: Research and Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 13/607,961

(22) Filed: Sep. 10, 2012

(65) Prior Publication Data

US 2013/0079503 A1 Mar. 28, 2013

(30) Foreign Application Priority Data

Sep. 8, 2011 (KR) .................. 10-2011-0091054

(51) Int. Cl.
- *C07F 5/00* (2006.01)
- *C02F 1/28* (2006.01)
- *C07F 7/10* (2006.01)
- *C07D 493/22* (2006.01)

(52) U.S. Cl.
CPC ................ *C07F 5/00* (2013.01); *C07D 493/22* (2013.01)
USPC .............. 534/16; 424/9.1; 424/9.3; 424/9.35; 424/9.36; 424/9.42

(58) Field of Classification Search
USPC ............. 424/9.1, 9.3, 9.341, 9.35, 9.36, 9.42; 556/418, 9
See application file for complete search history.

(56) References Cited

U.S. PATENT DOCUMENTS

2012/0058054 A1* 3/2012 Na et al. ................. 424/9.35

FOREIGN PATENT DOCUMENTS

KR 10-2010-0120971 A 11/2010

OTHER PUBLICATIONS

Zhuang Liu et al. PEGylated Nanographene Oxide for Delivery of Water-Insoluble Cancer Drugs, JACS, 2008, 130, 10876-10877.*
Xiaoming Sun et al. Nano-Graphene Oxide for Cellaular Imaging and Drug Delivery, Nano Res. 1, 203-212, 2008.*
Yong Liu et al., "Biocompatible Graphene Oxide-Based Glucose Biosensors", Langmuir Letter, Mar. 2010, 26(9), pp. 6158-6160.
V. K. Singh et al., "In situ of graphene oxide and its composites with iron oxide", New Carbon Materials, vol. 24, Issue 2, Jun. 2009, pp. 147-152.
"Notice of rejection" dated Jan. 22, 2013 which was cited in Korean Counterpart Application No. 10-2011-0091054 (4 pages).

* cited by examiner

*Primary Examiner* — Michael G Hartley
*Assistant Examiner* — Jagadishwar Samala
(74) *Attorney, Agent, or Firm* — NSIP Law

(57) ABSTRACT

Disclosed herein is a GO-Gd-DTPA (gadolinium-diethylen-etriamine pentaacetic-graphene oxide) complex, which is formed by an ester bond of graphene oxide (GO) and gadopentetic acid (Gd-DTPA). Since the GO-Gd-DTPA can stably exist in the body because it has high stability in water, it is expected that it can be effectively used as an MRI contrast agent.

8 Claims, 2 Drawing Sheets

GO-GD-DTPA COMPLEX, PREPARATION METHOD THEREOF, AND MRI CONTRAST AGENT COMPRISING THE SAME

CROSS-REFERENCE TO RELATED APPLICATIONS

This application claims the benefit under 35 U.S.C. §119 (a) to Korean Patent Application No. 10-2011-0091054 filed on Sep. 8, 2011, in the Korean Intellectual Property Office, the entire disclosure of which is incorporated herein by reference for all purposes.

BACKGROUND OF THE INVENTION

1. Technical Field

The present invention relates to a GO-Gd-DTPA complex, a preparation method thereof, and an MRI contrast agent including the same, and, more particularly, to a novel GO-Gd-DTPA complex, the stability of which is improved because it has high dispersibility compared to conventional MRI contrast agents, a preparation method thereof, and an MRI contrast agent including the same.

2. Description of the Related Art

As imaging technologies for observing the inside of a human body to diagnose diseases early, there are X-ray imaging, computed tomography (CT), positron emission tomography (PET), and the like. However, such imaging technologies are problematic in that they cannot be used to diagnose patients that are anxious about genetic variation because the human body is irradiated with radioactive rays. Recently, magnetic resonance imaging (MRI), which is a technology for detecting and imaging energy generated when high-frequency energy is applied to an atomic nucleus and then removed, has rapidly increased in use because it is stable compared to conventional imaging technologies.

However, MRI needs a contrast agent in order to improve sensitivity and peculiarity. When a contrast agent is used, it is possible to observe internal organs, such as blood vessels, stomach, liver and the like, which are not easy to find during X-ray imaging, and it is possible to ascertain the difference between normal tissue and diseased tissue (tumor), thus enabling early diagnosis of various diseases.

Currently, as a contrast agent generally used in clinics, transition metal ions, such as gadolinium (Gd) ions, manganese (Mn) ions and the like, are generally used. Such transition metal ions have a low molecular weight and very strong toxicity, and thus research into converting the ions into a complex using a biocompatible polymer has been actively done. However, an MRI contrast agent has problems of a short half-life and cellular toxicity as before. Further, since an MRI contrast agent has low dispersibility, there is a problem in that it coagulates in the body at the time of injecting it into the body, thus forming particles.

As such, in order to effectively use MRI in the early diagnosis of diseases, it is actually required to develop an MRI contrast agent having low toxicity and high dispersibility and stability.

SUMMARY OF THE INVENTION

Accordingly, the present invention has been devised to solve the above-mentioned problems, and an object of the present invention is to provide a novel GO-Gd-DTPA complex, the stability of which is improved because it has high dispersibility compared to conventional MRI contrast agents, a preparation method thereof, and an MRI contrast agent including the same.

However, an object to be accomplished by the invention is not limited to the above-mentioned object, and other objects not mentioned will be understood by those skilled in the art from the following description.

In order to accomplish the above object, an aspect of the present invention provides a GO-Gd-DTPA (gadolinium-diethylenetriamine pentaacetic-eraphene oxide) complex, which is formed by an ester bond of graphene oxide (GO) and gadopentetic acid (Gd-DTPA).

Another aspect of the present invention provides a method of preparing a GO-Gd-DTPA (gadolinium-diethylenetriandne pentaacetic-graphene oxide) complex, including the steps of: dissolving gadopentetic acid (Gd-DTPA) and graphene oxide (GO) in an organic solvent; treating the GO-Gd-DTPA with DCC (dicyclohexylcarbodiimide) and DMAP (dimethylaminopyridine) to esterify the GO-Gd-DTPA; bonding the esterified GO-Gd-DTPA with the graphene oxide (GO) in nitrogen gas to form a GO-Gd-DTPA (gadolinium-diethytenetriamine pentaacetic-graphene oxide) complex: and separating the GO-Gd-DTPA complex using a filter.

In the method, the organic solvent may be DMF (dimethylformamide) or THF (tetrahydrofuran).

Still another aspect of the present invention provides an MRI contrast agent composition including the GO-Gd-DTPA complex.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
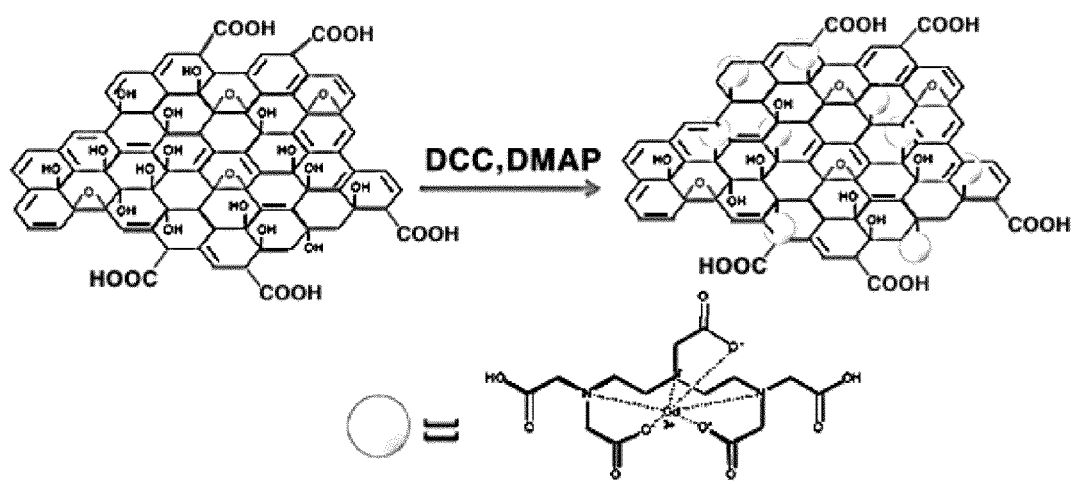
FIG. 1 is a schematic view showing a structure of GO-Gd-DTPA.
Figure 2:
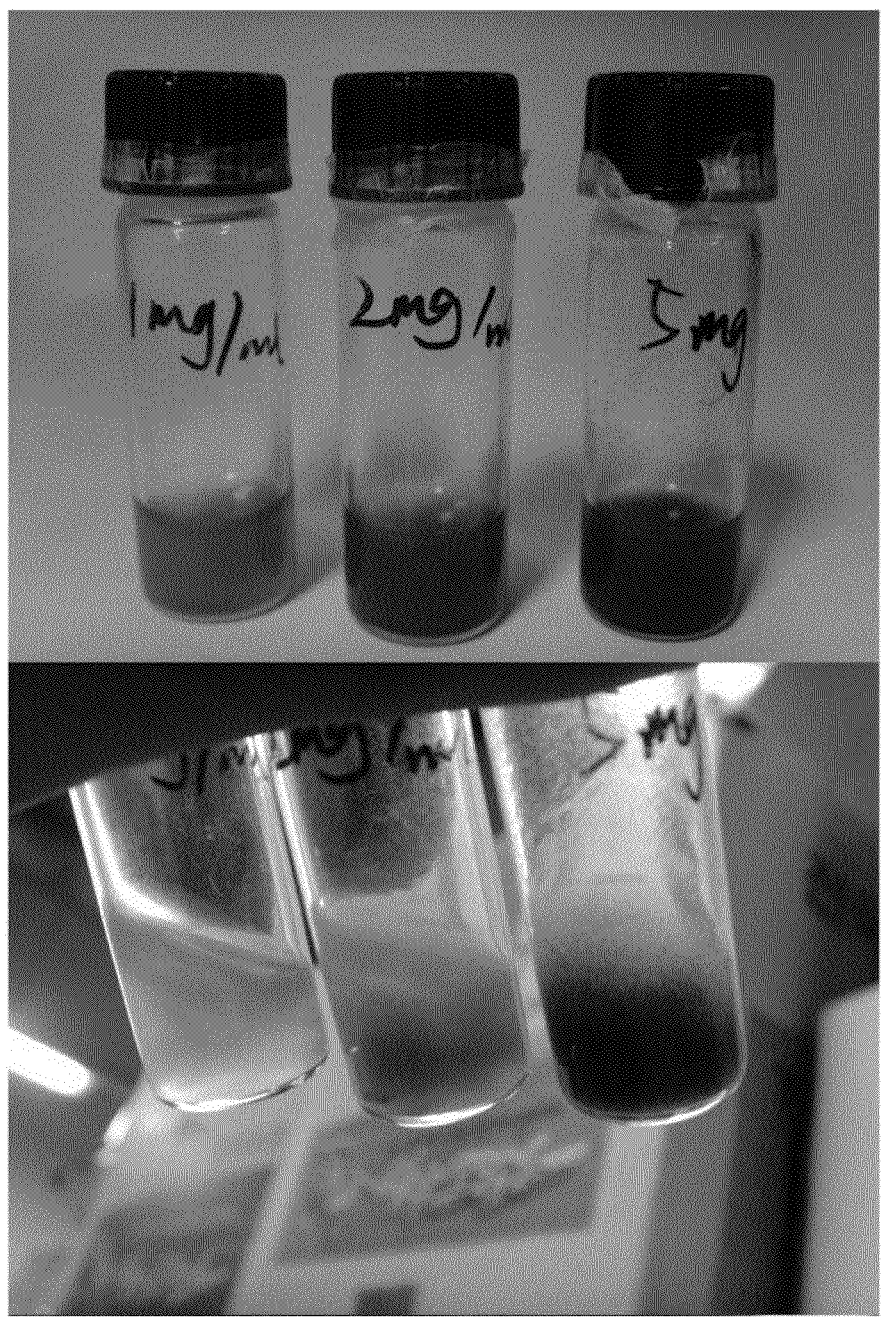
FIG. 2 is a photograph showing the results of a test of dispersibility of GO-Gd-DTPA.

Hereinafter, preferred embodiments of the present invention will be described in detail with reference to the attached drawings.

The present inventors researched an MRI contrast agent which does not cause cellular toxicity and which stably exists in the body because it has high dispersibility. As a result, the present invention was completed.

The present invention provides a GO-Gd-DTPA (gadoliniun-diethylenetriamine pentaacetic-graphene oxide) complex, which is formed by an ester bond of graphene oxide (GO) and gadopentetic acid (Gd-DTPA).

In order to prepare a complex which does not cause cellular toxicity and which is stably dispersed in the body, the present inventors bonded graphene oxide with Gd-DTPA (Magnevist™, manufactured by Bayer Co., Ltd.) which is a commonly-used gadolinium complex. Graphene oxide is widely used in the fields of polymers, ceramics, metals, thin films of electronic products, drug delivery, hydrogen storage, oil and gas recovery technologies, and the like because it is water soluble and has low toxicity. Further, graphene oxide is advantageous in that it can be produced in large quantities in an environment-friendly method.

The present invention provides a method of preparing a GO-Gd-DTPA (gadoliniurn-diethylenetriamine pentaaeetic-graphene oxide) complex, including the steps of: (a) dissolving gadopentetic acid (Gd-DTPA) and graphene oxide (GO) in an organic solvent; (b) treating the GO-Od-DTPA with DCC (dieyclohexylearbodiimide) and DMAP (dimethylaminopyridine) to esterify the GO-Gd-DTPA (c) bonding the esterified GO-Gd-DTPA with the graphene oxide (GO) in nitroen gas to form a GO-Gd-DTPA (gadalinium-diethylenanarnine pentaaectic-graphene oxide) complex; and (d) separating the GO-Gd-DTPA complex using a filter.

In the present invention, in order to bond Gd-DTPA with graphene oxide, Gd-DTPA is dissolved in DMF (dimethylformamide) and then treated with DCC and DMAP to activate a carboxylic group and thus esterify Gd-DTPA, and then the esterified Gd-DTPA is bonded with the graphene oxide (GO) to obtain a GO-Gd-DTPA complex. In the step of bonding Gd-DTPA with graphene oxide, any organic solvent can be used to dissolve both Gd-DTPA and graphene oxide as long as it does not prevent the bonding between Gd-DTPA and graphene oxide. The organic solvent may be DMF (dimethylformamide) or THF (tetrahydrofuran). The obtained GO-Gd-DTPA complex is separated using a nylon filter and then dried. In the step of separating the GO-Gd-DTPA complex, the GO-Gd-DTPA complex is washed with water and DMF to remove Gd-DTPA causing cellular toxicity, DMAP, DCC urea (final reaction product of DCC), and the like, thus increasing purity. As a result of analyzing the prepared GO-Gd-DTPA complex using ICP-OES/MS (Inductively Coupled Plasma Spectroscopy), it was ascertained that the amount of graphene oxide in the GO-Gd-DTPA complex was 4%.

According to an embodiment of the present invention, it was ascertained that the GO-Gd-DTPA complex had high dispersibility in an aqueous solution compared to a conventional MRI contrast agent (refer to Example 2).

Consequently, the GO-Gd-DTPA complex of the present invention can be used as an MRI contrast agent because it has high dispersibility. Therefore, the present invention provides an MRI contrast agent composition including the GO-Gd-DTPA complex.

The MRI contrast agent composition of the present invention can be formulated by a formulation method that is well known to those skilled in the art, and preferably, can be formulated into an intravenous injection or an oral administration.

The MRI contrast agent composition of the present invention may include a pharmaceutically allowable carrier. The pharmaceutically allowable carrier may include, but is not limited to, a physiological salt solution, polyethylene glycol, ethanol, vegetable oil and isopropyl myristate.

The dosage of the MRI contrast agent composition of the present invention may be suitably selected by those skilled in the art, although it is changed depending on the state and weight of a patient, the degree of a disease, the form of drug, the route of administration and the period of administration. Preferably, the contrast agent composition of the present invention is injected into the body in an amount of 0.001 to 100 mg/kg of body weight for 1 day, more preferably, 0.01 to 30 mg/kg of body weight for 1 day. The MRI contrast agent composition of the present invention may exist in an amount of 0.0001 to 10 wt %, preferably, 0.001 to 1 wt % based on the total amount thereof.

Hereinafter, the present invention will be described in more detail with reference to the following examples. However, these examples are set forth only to illustrate the present invention, and the scope of the present invention is not limited thereto.

EXAMPLES

Example 1

Method of Preparing a GO-Gd-DTPA Complex

Dicyclohexylcarbodiimide (DCC) (0.25 mg/mL) was added to Gd-DTPA (gadopentetic acid) (0.25 mg/mL) dispersed in dimethylformamide (DMF), and then reacted in nitrogen gas for 4 hours to activate a carboxylic group. Meanwhile, in the reaction, dimethylaminopyridine (DMAP) (0.1 mg/mL) was used as a catalyst for acyl group transfer. Graphene oxide (GO) was dispersed in DMF in a concentration of 2 mg/mL. The Gd-DTPA (20 mg/50 mL) and graphene oxide (100 mg/50 mL) dispersed in the DMF were mixed, and then stirred at room temperature for 2 hours to prepare a GO-Gd-DTPA complex. Thereafter, non-bonded Gd-DTPA and DMAP and DCC urea (final reaction product of DCC), were removed from the GO-Gd-DTPA complex using a nylon filter having a pore size of 0.2 μm to increase purity. In order to remove the non-bonded Gd-DTPA and DMAP and the DCC urea, the GO-Gd-DTPA complex was sequentially washed with 50 mL of deionized water three times, washed with 100 mL of DMF once, washed with 50 mL of deionized water three times, and then finally washed with 100 mL of acetone. Thereafter, the washed GO-Gd-DTPA complex was completely dried in a vacuum oven at 80° C. to obtain GO-Gd-DTPA complex powder.

Example 2

Dispersibility Test

In order to ascertain whether the prepared GO-Gd-DTPA complex can be stably used as an MRI contrast agent, the dispersibility thereof was measured. The GO-Gd-DTPA complex was dispersed in deionized (DI) water, and then observed for 24 hours. When the concentration of the GO-Gd-DTPA complex in DI water was 5 mg/mL, it was ascertained that particles settling down to the bottom were observed. Further, when the concentration thereof was 2 mg/mL, it was ascertained that particles settling down to the bottom were not observed. Furthermore, when the concentration thereof was 1 mg/mL, it was ascertained that the GO-Gd-DTPA complex was stably dispersed in deionized (DI) water due to the fact that crystals were not formed and its transparency was increased. The concentration of a conventional gadolinium complex, in which gadolinium is bonded with CNT (carbon nanotubes) in DI water to inject gadolinium into the body, was 1.2 mg/mL. Therefore, comparing the GO-Gd-DTPA complex of the present invention with the conventional gadolinium complex, it can be ascertained that the GO-Gd-DTPA complex of the present invention was stably dispersed in an aqueous solution compared to the conventional gadolinium complex.

As described above, since the GO-Gd-DTPA complex of the present invention can stably exist in the body because it has low toxicity and high dispersibility compared to a conventional gadolinium complex, it is expected that this GO-Gd-DTPA complex can be effectively used as an MRI contrast agent. Further, since the GO-Gd-DTPA complex of the present invention can be easily produced in a short period of time and oxide graphene can be produced in large quantities in an environment-friendly method, it is expected that this GO-Gd-DTPA complex can be used to produce an inexpensive MRI contrast agent in large quantities.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A GO-Gd-DTPA (gadolinium-diethylenetriamine pentaacetic-graphene oxide) complex, which is formed by an ester bond of graphene oxide (GO) and gadolinium-diethylenetriamine (Gd-DTPA) complex.

2. An MRI contrast agent composition, comprising the GO-Gd-DTPA complex of claim 1.

3. The GO-Gd-DTPA complex of claim 1, produced by:
   (a) dissolving gadolinium-diethylenetriamine pentaacetic (Gd-DTPA) complex and graphene oxide (GO) in an organic solvent;
   (b) treating the gadolinium-diethylenetriamine pentaacetic (Gd-DTPA) complex with dicyclohexylcarbodiimide (DCC) and dimethylaminopyridine (DMAP) to produce an esterified Gd-DTPA;
   (c) bonding the esterified Gd-DTPA with the graphene oxide (GO) in nitrogen gas to form a gadolinium-diethylenetriamine pentaacetic-graphene oxide (GO-Gd-DTPA) complex; and
   (d) separating the GO-Gd-DTPA complex using a filter.

4. The GO-Gd-DTPA complex of claim 3, wherein the organic solvent is dimethylformamide (DMF) or tetrahydrofuran (THF).

5. The MRI contrast agent composition, comprising the GO-Gd-DTPA complex of claim 4.

6. The MRI contrast agent composition, comprising the GO-Gd-DTPA complex of claim 3.

7. A method of preparing a GO-Gd-DTPA (gadolinum-diethylenetriamine pentaacetic-graphene oxide) complex, comprising the steps of:
   (a) dissolving gadopentetic acid (Gd-DTPA) and graphene oxide (GO) in an organic solvent;
   (b) treating the GO-Gd-DTPA with DCC (dicyclohexylcarbodiimide) and DMAP (dimethylaminopyridine) to esterify the GO-Gd-DTPA;
   (c) bonding the esterified GO-Gd-DTPA with the graphene oxide (GO) in nitrogen gas to form a GO-Gd-DTPA (gadolinum-diethylenetriamine pentaacetic-graphene oxide) complex; and
   (d) separating the GO-Gd-DTPA complex using a filter.

8. The method of claim 7, wherein the organic solvent is DMF (dimethylformamide) or THF (tetrahydrofuran).

* * * * *